United States Patent [19]

Boulogne et al.

[11] 4,421,128

[45] Dec. 20, 1983

[54] COMPACTED GREASELESS COSMETIC STICK AND PARTICULARLY STICK OF EYE SHADOW

[75] Inventors: Jean Boulogne, L'Hay-Les-Roses; Tibaud Hochmann, Champigny-s/Marne; Jacques Michelet, Longjumeau; Bruno Morane, Paris, all of France

[73] Assignee: L'Oreal, Paris, France

[21] Appl. No.: 12,518

[22] Filed: Feb. 15, 1979

Related U.S. Application Data

[63] Continuation of Ser. No. 703,362, Jul. 8, 1976, abandoned.

[51] Int. Cl.$^3$ ............................................. A45D 40/30
[52] U.S. Cl. ................................................... 132/88.5

[58] Field of Search ............................. 132/88.5, 88.7; 260/738, 23 R, 23.9, 28 R, 28.5 A, 28.5 B, 28.5 C, 28.5 D, 28.5 R; 401/49

[56] References Cited

U.S. PATENT DOCUMENTS

| | | | |
|---|---|---|---|
| 1,819,004 | 8/1931 | Roessinger | 132/88.5 |
| 2,226,377 | 12/1940 | Hart | 401/49 |
| 2,380,126 | 7/1945 | Sturm | 260/738 |

Primary Examiner—Gregory E. McNeill
Attorney, Agent, or Firm—Brisebois & Kruger

[57] ABSTRACT

Substantially greaseless cosmetic stick, particularly for applying eye shadow, comprises a carrier of compacted powder made of materials softer than calcium carbonate having a particle size between 1 and 20 microns, while its other constituents consist of powders having a particle size not greater than 25 microns.

11 Claims, No Drawings

COMPACTED GREASELESS COSMETIC STICK AND PARTICULARLY STICK OF EYE SHADOW

This is a continuation of application Ser. No. 703,362 now abandoned, filed July 8, 1976.

SUMMARY OF THE INVENTION

There are many known products for applying eye shadow to eyelids, that is to say, for applying a colored and/or nacreous layer to the lids so as to obtain an aesthetic effect. Cosmetic products of this type must, because of the sensitivity of the eyelids to make-up, be so gently applicable that the user feels no disagreeable sensation while the make-up is being applied. It is also desirable that the product be available in a form facilitating its use.

Eye shadows for application to the eyelids are presently known which permit an indirect application, that is to say, an application by means of an applicator which may be a pencil, a puff, or the finger of the user. An important part of these indirect eye shadows are powders, which may or may not be compacted, and which are supplied in cups or bottles. When the powders are compacted, the compacted product within the cup is not at all solid outside of its carrier so that it may be easily removed and the passage of the applicator over the compacted product picks up a sufficient quantity of the powder to insure the application of an adequate supply of eye shadow to the eyelids.

However, this method of operation has a disadvantage because the eyeshadow powders fall off the applicators during use and this results in a substantial loss and soiling of the clothing.

In order to avoid this disadvantage of indirect application, it has been suggested that direct eye shadows be used in the form of a stick or pencil permitting the user to apply the product directly to the area to be shadowed. For this purpose it is necessary for the cosmetic product to be in a solid form with sufficient resistance to breakage during the course of application. The compacted powder compositions used in indirect application cannot be used for direct application because these powders have practically no cohesive strength if they are at the same time easy to remove from the cup. Cosmetic products having different compositions have therefore been provided.

A first type of directly applied eye shadow consists of sticks or pencils having a greasy composition. That is to say, comprising a greasy binder in which the coloring pigments and other additives of the composition are dispersed. These products are in general poured while hot into their final shape and permit their application with sufficient gentleness because of the presence of the greasy substance which provides an agreeable sensation at the moment of application. However, their durability is dependent upn the ambient temperature which may lead to regrettable results if the temperature is too high, because the grease-based products cause excessive softening of the stick or the destruction of the pencil. Moreover, the retention of the make-up on the eyelids is not satisfactory and the greasier the eyelids the more true this is. The make-up decomposes and loses its homogeneity and the greasy colored paste runs into the folds in the eyelids.

To avoid the disadvantages of greasy make-up it has also been suggested that direct make-up sticks be provided which are called "chalks". These chalks are, in general, obtained by molding or extrusion from a paste which is dried after shaping as is indicated, for example, in U.S. Pat. No. 3,800,034. The compositions used for the manufacture of these chalks contain in general 40 to 90% calcium carbonate, which makes them very comparable to the chalks used to write on a blackboard. The disadvantages of this type of product result from the fact that the make-up chalks are either sufficiently strong so that they don't break during application, in which case they do not adhere well to the eyelids, or, while they adhere well to the eyelids, they are too fragile and break during use. In both cases, the presence of a substantial quantity of calcium carbonate gives the user a disagreeably rough impression at the moment of application.

It is the object of the present invention to describe a stick of eye make-up obtained by compacting a powder which avoids the disadvantages of all the known products. This stick according to the invention is of the chalk type and permits direct application. It does not comprise any greasy supporting material so that constant application is permitted regardless of the temperature. It comes off the stick well enough to insure satisfactory application but it is nevertheless so strong that it does not break in the course of normal use. The application of the stick according to the invention to the eyelids produces a gentle agreeable sensation during application despite the strength of the stick. The fact that the stick according to the invention permits direct application avoids the disadvantages inherent in the use of applicators and in particular any soiling due to the falling off of particles of the cosmetic product which become separated from the applicator.

It is accordingly an object of the present invention to provide, as a new article of manufacture, a make-up stick of the chalk type particularly designed for the direct application of eye shadow to the eyelids, said stick being constituted by a substantially greaseless carrier containing make-up pigments characterized by the fact that it consists of a powder which is compacted while dry under pressure, and which contains about 25 to 70% of at least one powder constituting the said greaseless carrier, said powder having substantially rounded grains, the average diameter of which is between about 1 and 20 microns, the compacted supporting grains at ambient temperature under a pressure of 120 bars having a hardness less than that of compacted calcium carbonate under the same conditions.

In a preferred embodiment of the invention the powdered products (other than those forming the carrier) which are present in the composition have grains the average diameter of which is less than about 25 microns. The powdered product or products forming the carrier constitute 30 to 50% by weight of the composition of the stick. The powdered product constituting the carrier has grains the average diameter of which lies between 5 and 10 microns. The powdered product constituting the carrier is selected from the group of starches consisting of rice starch, corn starch, esterified rice starch, and esterified corn starch, polymeric powders, and particularly polyamide powders. The polyamide powders which may be used to constitute the carrier are preferably selected from the polymeric powders obtained from the lactam of 12-aminododecanoic acid sold under the trademark NYLON 12. For a cylindrical stick having a length between 2.5 cm and 2.7 cm, the compacting pressure on the powder is between 350 and 1200 bars. The stick material contains colored pigments in a proportion between 5 and 25% by weight. The stick may contain perfume in a proportion of between 0.1 and 2% by weight about. The stick material contains fillers such as talc, and/or calcium carbonate in a proportion less than 30% by weight and contains products improving the opacity of the layer of make-up in a proportion less than 10% by weight. The products improving the opacity of the layer of make-up are selected from the group formed by titanium dioxide, zinc oxide, and kaolin. The stick material contains at least one product improving the adherence of the make-up in a proportion between 0.5 and 2% by weight. The products improving the adherence of the make-up are metallic stearates and preferably zinc, calcium, magnesium or aluminum stearates. The stick material may contain at least one product imparting a satin or nacreous effect in a proportion between 5 and 40% by weight. The products producing a satin or nacreous effect are selected from the group consisting of bismuth oxychloride, titanium mica and aluminum powder.

It has been found that when one utilizes in the stick according to the invention a powdered carrier such as the one above described, it is possible to obtain, after compacting, a stick having a resistance to shear stress sufficient to avoid any breakage during normal application of make-up. The compacting pressures to be used are variable in dependence upon the dimensions of the stick and may be easily determined by the man skilled in the art but the surprising character of the invention results from the fact that one may, nevertheless, with such a carrier, obtain simultaneously a strong compacted stick and a stick which rubs off readily during the application of the make-up and gives the user an agreeable gentle sensation. The greaseless carriers heretofore used never made it possible to simultaneously obtain both of these advantages.

For the dimensions of the stick and the compacting pressures indicated in the preferred embodiment of the invention the resulting stick has a resistance to shear stress between 1100 g/cm$^2$ and 1800 g/cm$^2$. If the sticks according to the invention are applied with a force of 50 g to the skin or to an analogous surface it has been found that at a speed of movement of 0.3 cm/sec, there is deposited upon said suface a quantity of the make-up comprised between about 0.4 mg/cm$^2$ and 0.8 mg/cm$^2$. The numerical information given above clearly indicates that the stick according to the invention has both a suitable strength and a suitable ability to rub off on the skin.

It is believed, without limiting the scope of the invention thereto, that the gentleness of application results simultaneously from the dimensions of the grains of the powder of the carrier and the softness of the material constituting the carrier while the strength of the compacted stick and its satisfactory ability to rub off on the skin results from the substantially rounded shape of the grains of the powder of the carrier and the range of dimensions chosen for these grains.

In order that the object of the invention may be better understood, several embodiments thereof will now be described purely by way of illustration and example. In the following examples, all the formulas are given in terms of parts by weight.

EXAMPLE 1

The following formulation was prepared:
Esterified rice starch: 50%
Calcium carbonate: 15%
Talc: 12%
Magnesium stearate: 1%
Titanium oxide: 2%
Zinc oxide: 3%
Anhydrous chromium oxide: 11%
Yellow iron oxide: 4%
Black iron oxide: 2%

In this formulation the esterified rice starch is a powder having an average diameter of 5 microns, the extreme dimensions being about 1 and 7 microns. All the other powders consist of grains having average diameters less than 20 microns.

An intimate mixture of the various components in a mixer is prepared for 30 minutes and the mixture is then passed through a screen having an average distance of 100 microns between the wires. The product is then compacted into cylindrical sticks 2.7 cm long and 11.2 mm in diameter at a compacting pressure of 350 bars. The resulting stick has a shear strength of 1550 g/cm$^2$ (shear force exerted at 16 mm from the usable end of the stick). Under an application pressure of 50 g and with a speed of movement of the support of 0.3 cm/sec, using a paper carrier having a surface texture analogous to that of eyelid skin, a deposit of 0.4 mg/cm$^2$ resulted. The make-up obtained had a flat yellow-green tint. The stick felt very soft during application to the eyelids.

EXAMPLE 2

The following formulation was prepared:
Esterified rice powder: 30%
NYLON 12 powder: 20%
Zinc stearate: 1%
Titanium oxide: 2%
Zinc oxide: 3%
Bismuth oxychloride: 27%
Ultramarine blue: 1%
Anhydrous chromium oxide: 16%

The esterified rice starch powder utilized in this formulation is the same as the one defined in Example 1. The NYLON 12 powder has an average grain diameter of 8 microns and its extreme dimensions are about 2 and 12 microns. The other powders in the formulation have diameters less than 25 microns. The method of operation is the same as that described in Example 1. The product was compacted into cylindrical sticks 2.7 cm long and 11.2 mm in diameter at a compacting pressure of 560 bars.

This produced a compacted stick having a shear strength of 1830 g/cm$^2$ (measured under the conditions indicated in Example 1) and which rubs off at the rate of 0.75 mg/cm$^2$. This stick permits a green satin tint to be obtained and is very gentle in application.

EXAMPLE 3

The following formulation is prepared:
NYLON 12 powder: 30%
Talc: 8%
Calcium stearate: 1%
Bismuth oxychloride: 32%
Titanium mica: 8%
Ultramarine blue: 7%
Anhydrous chromium oxide: 14%

The NYLON 12 powder has the same characteristics as that used in Example 2. An intimate mixture of the various constituents is prepared, except for the titanium mica, in a mixer for 30 minutes and the resulting mixture is passed through a screen having a mesh opening of 100 microns.

It is then returned to the mixer and the titanium mica is introduced so as to produce a homogenous mixture and this mixture is passed through a screen having a mesh opening of 160 microns. The product is then compacted in the form of sticks having the same dimensions as indicated in Example 1 with a compacting pressure of 560 bars under the conditions indicated in Example 1. The result is a stick having a shear strength of 1100 g/cm$^2$ and which rubs off at the rate of 0.70 mg/cm$^2$. This stick produces a nacreous turquoise tint and goes on very smoothly.

EXAMPLE 4

The following formulation is prepared:
Corn starch: 40%
Aluminum stearate: 1.5%
Bismuth oxychloride: 20%
Titanium mica: 10%
Talc: 12%
Yellow iron oxide: 10%
Red iron oxide: 6%
Black iron oxide: 0.5%

The corn starch powder has an average diameter of about 10 microns, the extreme dimensions being about 6 and 18 microns. The method of operation used in this example is the same as given in Example 3. The product is compacted into cylindrical sticks 2.5 cm long and 11.2 mm in diameter at a compacting pressure of 1200 bars. Under the test conditions which have been indicated in Example 1 it has been determined that the stick has a shear strength of 1550 g/cm$^2$ and rubs off at 0.78 mg/cm$^2$. This stick produces a nacreous squirrel brown tint and is very smooth in its application.

It will of course be appreciated that the embodiments which have been described have been given purely by way of illustration and example and may be modified as to detail without thereby departing from the basic principles of the invention.

What is claimed is:

1. A greaseless make-up stick of the chalk type which is particularly adapted for direct application to the eyelids, said greaseless make-up stick comprising a dry compacted admixture of
    (1) 25–75% of a greaseless carrier powder,
        (a) which has substantially rounded grains, the average diameter of which is between 1 and 20 microns, and
        (b) which is selected from the group consisting of rice starch, corn starch and esterified rice starch, esterified corn starch and polyamide powders, and
    (2) at least one make-up pigment,
said compacted admixture having a hardness less than calcium carbonate when compacted at room temperature and under a pressure of 120 bars.

2. The make-up stick of claim 1 in which the powders other than those forming the carrier which are present in the composition are in the form of grains having an average diameter less than 25 microns.

3. The make-up stick of claim 1 in which the powder forming the carrier constitutes 30 to 50% by weight of the composition of the stick.

4. The make-up stick of claim 1 in which the powder constituting the carrier has grains, the average diameter of which is between 5 and 10 microns.

5. The make-up stick of claim 1 in which the powder constituting the carrier is selected from the group consisting of rice starch, corn starch and esterified rice starch, esterified corn starch and polyamide polymers.

6. The make-up stick of claim 1 which also contains from 5 to 25% by weight of colored pigments.

7. The make-up stick of claim 1 containing filler powders in a proportion less than 30% by weight.

8. The make-up stick of claim 1 which also contains products for increasing the opacity of the make-up layer selected from the group consisting of titanium dioxide, zinc oxide and kaolin in a proportion of less than 10% by weight.

9. The make-up stick of claim 1 which also contains at least one product for improving the adherence of make-up in a proportion between 0.5 and 2% by weight.

10. The make-up stick of claim 1 which also contains at least one product producing a satin or nacreous effect, selected from the group consisting of bismuth oxychloride, titanium mica, and aluminum powder, in a proportion between 5 and 40% by weight.

11. The make-up stick of claim 1 which also contains from 0.1 to 2% by weight of perfume.

* * * * *

UNITED STATES PATENT AND TRADEMARK OFFICE
CERTIFICATE OF CORRECTION

PATENT NO. : 4,421,128
DATED : December 20, 1983
INVENTOR(S) : Jean Boulogne et al.

It is certified that error appears in the above-identified patent and that said Letters Patent is hereby corrected as shown below:

Please correct the spelling of the first name of the second inventor:

[75] Thibaud Hochmann

On the title page insert:

-- [30] Foreign Application Priority Data

July 16, 1975 /FR/ France....75 22207 --.

Signed and Sealed this

Fourteenth Day of February 1984

[SEAL]

Attest:

GERALD J. MOSSINGHOFF

Attesting Officer

Commissioner of Patents and Trademarks